United States Patent [19]

Skardoutos et al.

[11] Patent Number: 5,139,526
[45] Date of Patent: Aug. 18, 1992

[54] LONG ABOVE ELBOW AND ELBOW DISARTIC PROSTHESIS

[75] Inventors: James Skardoutos; Dominic Lemma, both of Royal Oak, Mich.

[73] Assignee: Wright & Filippis, Inc., Rochester, Mich.

[21] Appl. No.: 597,375

[22] Filed: Oct. 12, 1990

[51] Int. Cl.⁵ .............................................. A61F 2/58
[52] U.S. Cl. ........................................ 623/59; 623/39; 623/33
[58] Field of Search .................... 623/57–60, 623/38, 39, 44, 33

[56] References Cited

U.S. PATENT DOCUMENTS

| | | | |
|---|---|---|---|
| 2,800,345 | 7/1957 | Goodwin et al. | 623/57 X |
| 2,944,846 | 7/1960 | Jones | 623/57 X |
| 3,526,007 | 9/1970 | Iuko et al. | 623/58 |
| 3,900,900 | 8/1975 | Horvath | 623/38 X |
| 4,216,550 | 8/1980 | Thompson | 623/38 X |
| 4,274,165 | 6/1981 | Iuko et al. | 623/57 |
| 4,520,512 | 6/1985 | Lehneis et al. | 623/39 |
| 4,564,365 | 1/1986 | Winer et al. | 623/38 X |
| 4,614,518 | 9/1986 | Lehneis et al. | 623/39 |

FOREIGN PATENT DOCUMENTS

| | | | |
|---|---|---|---|
| 0326422 | 9/1920 | Fed. Rep. of Germany | 623/57 |
| 1030508 | 5/1958 | Fed. Rep. of Germany | 623/39 |
| 0247459 | 7/1969 | U.S.S.R. | 623/57 |
| 0596206 | 12/1947 | United Kingdom | 623/57 |
| 0978586 | 12/1964 | United Kingdom | 623/38 |
| 1006953 | 10/1965 | United Kingdom | 623/58 |

Primary Examiner—Randall L. Green
Assistant Examiner—D. Willse
Attorney, Agent, or Firm—Harness, Dickey & Pierce

[57] ABSTRACT

A prosthesis has a humeral member, rotating elbow member and forearm member. The prosthesis provides rotational and up and down vertical movement of the forearm with respect to the humeral member while being anatomically proportional with the amputee's sound arm.

14 Claims, 3 Drawing Sheets

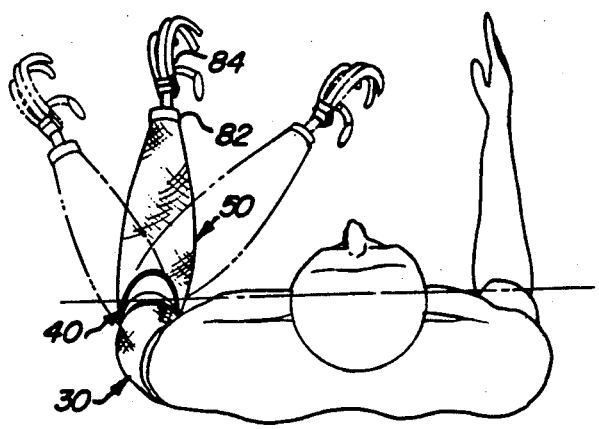
*Fig-4A*
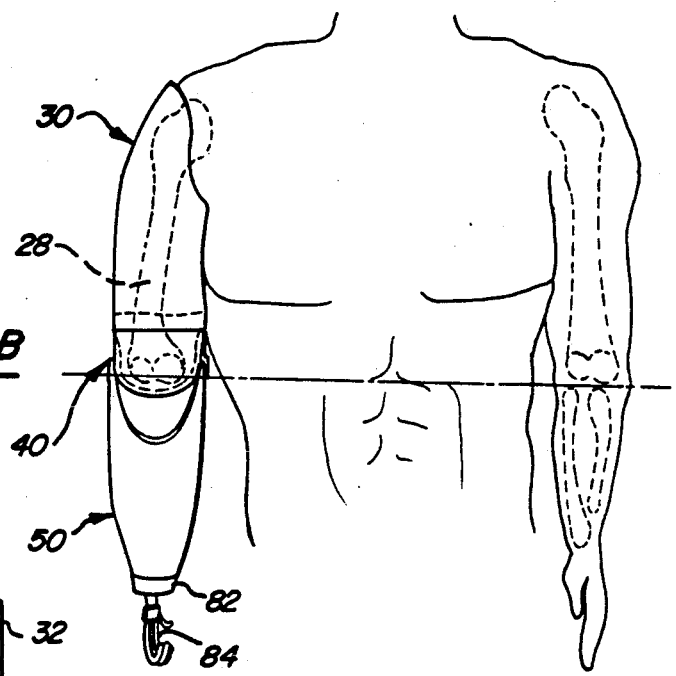
*Fig-4B*
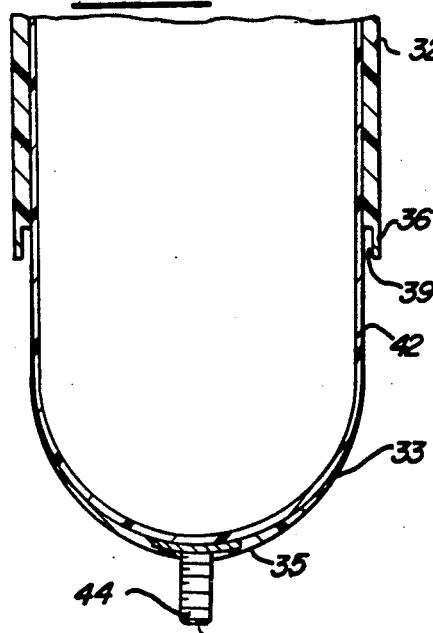
*Fig-5*
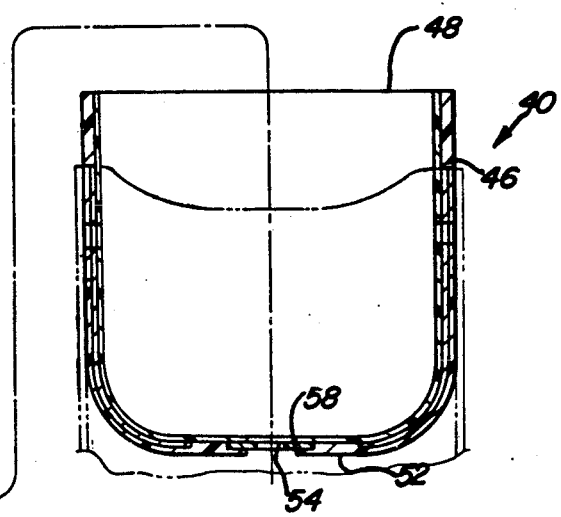

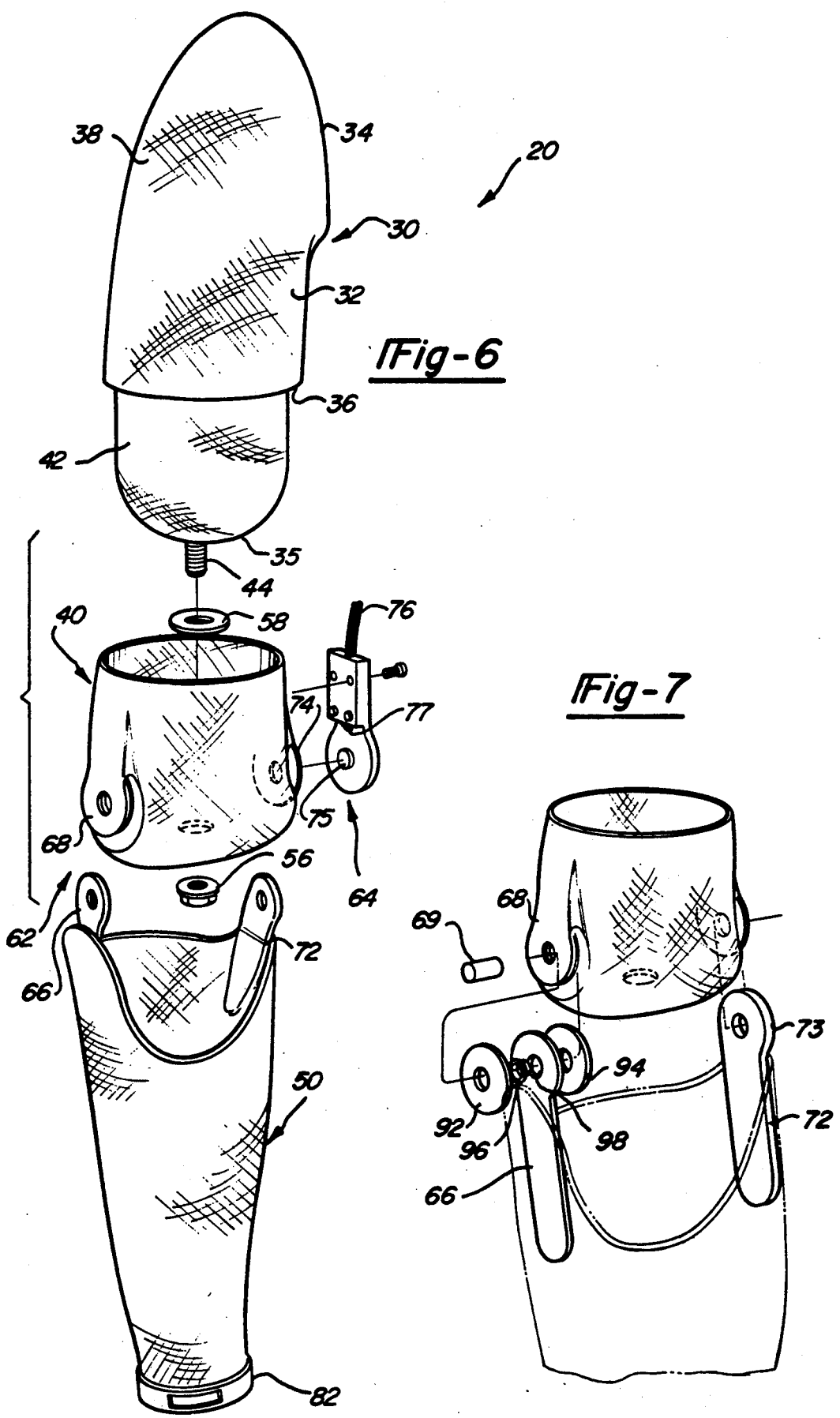

LONG ABOVE ELBOW AND ELBOW DISARTIC PROSTHESIS

BACKGROUND OF THE INVENTION

The present invention relates to prosthetic devices and, more particularly, to long above elbow and elbow disartic prosthesis.

Generally, prostheses are utilized to restore function or to achieve a cosmetic reconstruction of a superficial feature of the body. Due to trauma or disease, it is sometimes necessary or appropriate treatment to surgically remove portions of the body such as a whole limb, a segment of a long bone, or inner faces of a joint. In many cases, such body components can be replaced by components or devices which restore appearance and some limited function.

When the forearm is disarticulated or severed above the elbow, the amputee is left with a substantial stump. A prosthesis is ordinarily provided which is affixed to the stump and provides the amputee with a device which restores appearance and some limited function. Devices which are currently commercially available while appearing to function satisfactorily, have disadvantages.

Turning to FIG. 1, a commercially available prosthesis is shown. Generally, the prosthesis includes a humeral structure 1, an internal locking elbow 2, a forearm structure 3 and a terminal device 4. This particular type of device is best utilized when the arm has been severed well above the elbow. When the device of FIG. 1 is utilized on a stump severed well above the elbow, the device enables the elbow joint 2 to be aligned with the elbow of the amputee's sound arm. In the event of a long above elbow amputation or elbow disarticulation, this type of device positions the prosthesis elbow well below the elbow of the amputee's sound arm and the prosthesis terminal device extends a substantial distance beyond the amputee's sound hand. Thus, it is desirable to provide a prosthesis which may be fitted such that regardless of the type of amputation, the elbow of the prosthesis may be anatomically aligned with the elbow of the amputee's sound arm to provide an anatomically proportional aesthetic appearance.

Accordingly, the present invention provides the art with such a device. The prosthesis of the present invention provides the art with a forearm which is rotatable with respect to the humeral portion of the arm. The present invention provides a forearm which may be moved up and down and releasably locked in several positions. The present invention provides a prosthesis which may be anatomically matched with the amputee's sound arm regardless of the particular type of amputation to provide an aesthetic appearance.

From the subsequent detailed description taken in conjunction with the accompanying drawings and claims, other objects and advantages of the present invention will become apparent to those skilled in the art.

BRIEF DESCRIPTION OF THE DRAWINGS

FIG. 4A is a top plan view of the prosthesis in accordance with the present invention on an amputee.

FIG. 4B is a front elevation of the prosthesis of FIG. 4A on an amputee.

FIG. 5 is an exploded sectional view of the elbow joint of the present invention.

FIG. 6 is an exploded perspective views of the prosthesis in accordance with the present invention.

FIG. 7 is an exploded perspective view of the elbow of FIG. 6.

DETAILED DESCRIPTION OF THE PREFERRED EMBODIMENT

Figure 1:
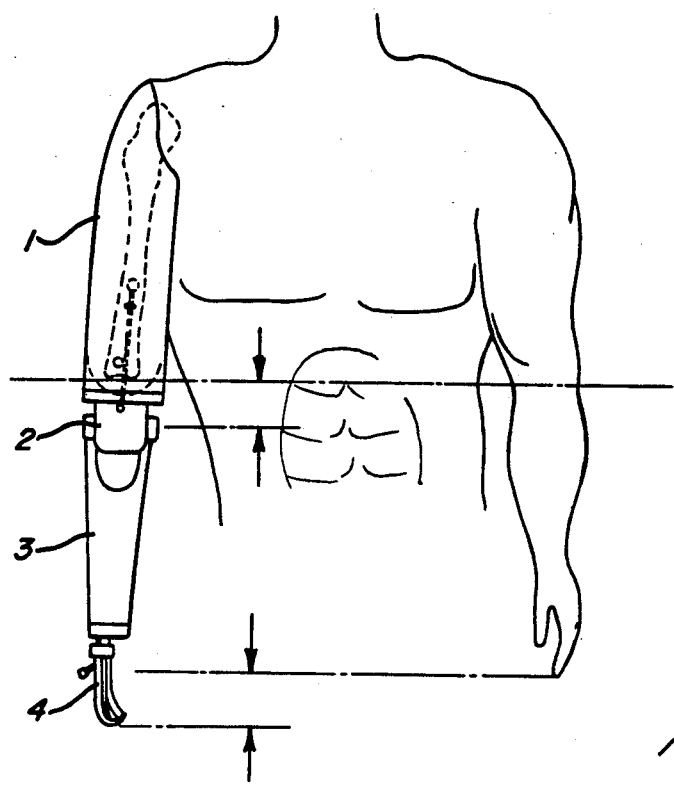
FIG. 1 illustrates a front elevation view of an existing prosthesis.
Figure 2:
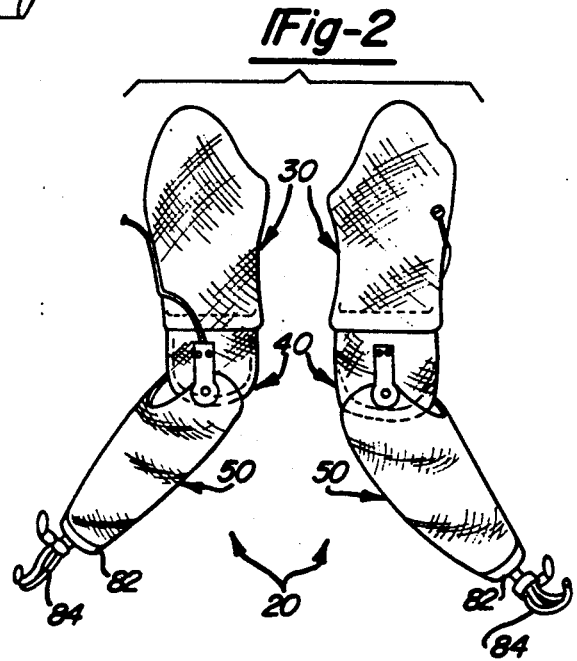
FIG. 2 illustrates a medial and lateral elevation view of a prosthesis in accordance with the present invention.

Referring to FIGS. 2 through 7, a prosthesis is illustrated and designated with the reference numeral 20. The prosthesis 20 is utilized on long above elbow amputations and elbow disartics. Generally, the prosthesis 20 includes a first humeral member 30, a second rotating elbow member 40 and a movable forearm member 50.

The humeral member 30 has an overall cylindrical tubular shape designed to emulate the humeral portion of an amputee's stump 28. The humeral member 30 includes a cylindrical wall 32 defining a hollow interior with an end opening 34 enabling the stump 28 to insert into the interior and with a continuous arcuate bottom 33 having a concave exterior surface 35. The humeral member 30 also includes a flange overlap 36 positioned generally below the mid point of the humeral member 30. The flange overlap 36 is continuous with the upper portion 38 of the humeral member 20. A gap 39 is formed between the flange overlap 36 and the surface of the bottom portion 42 of the humeral member 30. The gap enables the rotating elbow member 40 to rotatably position onto the bottom portion 42 and insert into the gap 39 to provide a pleasing aesthetic appearance. Also, a stud 44 extends from the concave exterior surface 35 of the humeral member 30. The stud 44 may be threaded and is utilized to retain the rotating elbow member 40 onto the humeral member 30 as will be explained herein.

The rotating elbow member 40 has an overall cup shape adapted to fit over the lower end portion 42 of the humeral member 30. The rotating elbow member 40 includes a cylindrical wall 46 having an open end 48 and an arcuate concave bottom end exterior surface 52. The rotating elbow member 40 has a hollow interior corresponding in shape to the lower portion 42 of the humeral member 30 as seen in FIG. 5. Thus, the rotating elbow member 40 is positioned over the lower portion 42 of the humeral member 30 with the opened end edge 48 positioned under the flange overlap 36 as seen in FIG. 5. The stud 44 projects through an aperture 54 in the bottom 52 of the rotating elbow member 40 to enable a retaining fastener 56 to secure the rotating elbow member 40 onto the humeral member 30. A washer 58 may be positioned on the interior surface of the rotating elbow member 40 to provide a friction surface. As can be seen in FIG. 4A, the rotating elbow member 40 may be rotated medially and laterally to provide for rotational movement of the forearm 50 with respect to the humeral member 30. The rotating elbow member 40 and humeral member 30 are sized such that they are anatomically proportioned to the amputee's sound arm so that the position of the rotating elbow member 40 is substantially at about the elbow position of the sound arm as seen in FIGS. 4A and B.

Figure 3:
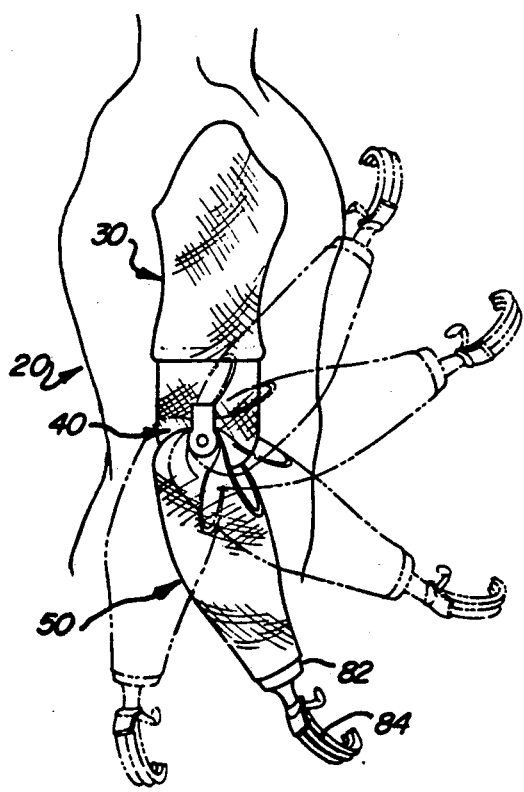
FIG. 3 is a lateral side elevation view of the prosthesis of FIG. 2 illustrating up and down movement in phantom.

The rotating elbow member 40 also includes a pair of hinge mechanisms 62 and 64 to retain the forearm member 50 to the rotating elbow member 40. The hinge mechanism 62 includes a pair of leaves 66 and 68 joined by a pin 69 to provide free movement of the hinge mechanism 62. Also, a pair of washers or spacers 92 and 94 flank leaf 66 to provide friction surfaces. A bushing 96 is positioned in an aperture 98 of leaf 66 to provide for pivoting of the leaves 66 and 68 as seen in FIG. 7. Hinge mechanism 64 is of the locking type having a pair of leaves 72 and 74 joined by a pin 75. Hinge member 72 has a plurality of notches on its head 73 which act with a pawl 77. A locking cable release 76 includes the pawl 77 so that as the forearm 50 is moved vertically up and down it can be selectively locked into position as seen in FIG. 3. The cable 76 enables the release of the locking hinge 64 to enable additional positioning of the forearm 50 as seen in FIG. 3.

The forearm 50 has an overall truncated conical shape emulating the shape of the amputee's sound forearm. The forearm may include a wrist unit 82 and a terminal device 84. The forearm 50, with the wrist unit and terminal device 82 and 84, is anatomically proportionate to the amputee's sound arm to provide the amputee with a prosthesis and sound arm which are of substantially the same length to provide symmetry to the amputee's upper body as seen in FIGS. 4A and B.

The present prosthesis may be positioned onto a long above elbow amputation or elbow disarticulation and provide the amputee with an anatomically proportional prosthesis. The rotating elbow member 40 is positioned with respect to the sound arm at substantially the elbow center and axis of up and down movement on substantially the same axis as seen in FIG. 4B. Thus, this provides the amputee with a prosthesis that is symmetrical with respect to his body and eliminates the undesirable effect of having one arm longer than the other.

While the above provides a detailed description of the preferred embodiment of the present invention, it will be understood that the invention is susceptible to modification, variation and alteration without deviating from the scope and true meaning of the subjoined claims.

What is claimed is:

1. A prosthesis comprising:
   a first member adapted to be secured onto a stump;
   a second member movably coupled with said first member, said second member including a rotation means for providing rotatable movement of said second member with said first member, said rotation means including a cup member, said cup member including a wall having an open end for receiving and surrounding a portion of said first member and adapted to surround a portion of the stump, said cup member rotatably secured to said first member by a fastening means, said first and second members emulating a sound human limb.

2. The prosthesis according to claim 1 wherein said fastening means includes a stud extending from said first member through an aperture in said cup member and a retaining member coupled with said stud to secure said cup member to said first member.

3. The prosthesis according to claim 1 wherein said second member further includes a hinged portion to provide the second member with additional movement.

4. The prosthesis according to claim 1 wherein said cup member surrounds a lower end portion of said first member.

5. The prosthesis according to claim 1 wherein once said first member is secured to the stump, said first and second members are substantially anatomically proportional with the amputee's sound limb.

6. A prosthesis for disarticulated or long elbow amputations comprising:
   a humeral member adapted for positioning over and securing with an arm stump, said humeral member having an exterior surface;
   a rotating elbow member surrounding a portion of said exterior surface of said humeral member, said rotating member coupled with said humeral member, said elbow member having a cylindrical wall having an open end for receiving a portion of said humeral member and adapted to surround a portion of the stump; and
   a forearm member hinged for movement with said rotating member, said humeral, rotating elbow and forearm members being of desired adjustable sizes such that the prosthesis is adapted to be substantially anatomically proportional with an amputee's sound arm.

7. The prosthesis according to claim 6 wherein said humeral member includes a radial overlap covering an edge portion of said rotating elbow member.

8. The prosthesis according to claim 6 wherein said rotating elbow member has an overall cup shape with annular wall having two ends, one end being open and the other being continuous and arcuate.

9. The prosthesis according to claim 6 further comprising a wrist member secured to said forearm member.

10. The prosthesis according to claim 9 further comprising a terminal device secured to said wrist member.

11. A prosthesis for disarticulated or long elbow amputations comprising:
    a humeral member adapted to be connected with an arm stump;
    a rotating elbow member surrounding a portion of said humeral member and adapted to surround a portion of the stump and providing the prosthesis with rotational movement, said rotating elbow member including a cylindrical wall open at one end and the other end being arcuate and continuous therewith, said humeral member end portion inserting into said open end and abutting the arcuate end, a stud extending from said humeral member through an aperture in said rotating elbow member with a retaining member on said stud to secure said rotating elbow member with said humeral member; and
    a forearm member coupled with said rotating elbow member by a hinge means for hinged movement.

12. The prosthesis according to claim 11 wherein said hinge means includes a pair of hinges connecting said rotating elbow member with said forearm member.

13. The prosthesis according to claim 12 wherein one of said hinges is of a releasable locking type hinge enabling the forearm member to be moved vertically and locked in a plurality of positions.

14. The prosthesis according to claim 11 wherein said stud is threaded and said retaining member includes a mating threaded nut for maintaining coupling of the rotating elbow member with the humeral member.

* * * * *